(12) United States Patent
Fischer et al.

(10) Patent No.: US 6,204,417 B1
(45) Date of Patent: Mar. 20, 2001

(54) METHOD FOR PRODUCING ALIPHATIC ALCOHOLS

(75) Inventors: Rolf Fischer, Heidelberg; Rolf Pinkos, Bad Dürkheim; Joachim Wulff-Döring, Frankenthal, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,876

(22) PCT Filed: May 12, 1998

(86) PCT No.: PCT/EP98/02777
§ 371 Date: Nov. 15, 1999
§ 102(e) Date: Nov. 15, 1999

(87) PCT Pub. No.: WO98/52891
PCT Pub. Date: Nov. 26, 1998

(30) Foreign Application Priority Data
May 16, 1997 (DE) ............................................. 197 20 657

(51) Int. Cl.$^7$ ........................... C07C 31/18; C07C 31/24; C07C 29/136; C07C 27/04
(52) U.S. Cl. ......................... 568/853; 568/864; 568/875; 568/885
(58) Field of Search ................................. 568/853, 864, 568/875, 885

(56) References Cited

U.S. PATENT DOCUMENTS

| 4,108,478 | * | 8/1978 | Trivedi | 568/885 |
| 4,214,106 | * | 7/1980 | Freudenberger | 568/864 |
| 4,338,221 | * | 7/1982 | Qualeatti | 502/241 |
| 4,398,039 | * | 8/1983 | Pesa et al. | 560/265 |
| 4,985,572 | * | 1/1991 | Kitson et al. | 549/326 |

FOREIGN PATENT DOCUMENTS

| 2715667 | 10/1978 | (DE) . |
| 417867 | 9/1995 | (EP) . |
| 1551741 | 8/1979 | (GB) . |

OTHER PUBLICATIONS

Yoshino et al, *JAOCS*, vol. 67, No. 1, Jan. 1990, pp. 21–24.

* cited by examiner

Primary Examiner—Johann Richter
Assistant Examiner—Brian J. Davis
(74) Attorney, Agent, or Firm—Keil & Weinkauf

(57) ABSTRACT

In a process for preparing aliphatic alcohols by hydrogenating aliphatic carboxylic acids or anhydrides or esters thereof or lactones in the presence of a catalyst comprising Pt and Re, in the form of the metal or an oxide in each case, the catalyst further comprises at least one further element from the groups 5 to 12 and 14 and the lanthanides of the Periodic Table of the Elements in the form of the metal or an oxide.

7 Claims, No Drawings

METHOD FOR PRODUCING ALIPHATIC ALCOHOLS

This application is a 371 of PCT EP 98/02777 filed May 12, 1998.

The present invention relates to a process for preparing aliphatic alcohols by hydrogenating aliphatic carboxylic acids or anhydrides or esters thereof or lactones in the presence of a catalyst.

Various processes for hydrogenating aliphatic carboxylic acids to give aliphatic alcohols are known.

The hydrogenation of hexanoic acid and decanoic acid to give the corresponding alcohols in the presence of a catalyst comprising $Re_2O_7$ and $OsO_4$ on a carbon support is described in K. Yoshino et al., "Hydrogenation of carboxylic acids by rhenium-osmium bimetallic catalyst", JAOCS 67 (1990), 21–24.

DE-A-27 15 667 describes a process for preparing 1,4-butanediol by hydrogenating maleic anhydride, maleic acid or fumaric acid using Pd and Re on a specific silicoacetate as catalyst. The reaction temperature is from 205 to 230° C.

EP-B-0 417 867 describes catalysts for hydrogenating carboxylic acids and anhydrides thereof to give alcohols or esters. The catalysts used include, for example, Pd, Pd/Re, Ag/Pd, Ag/Pd/Re on carbon. The conversions of acetic acid into ethanol and of maleic anhydride into gamma-butyrolactone are described. The reaction is carried out at from 194 to 251° C.

U.S. Pat. No. 4,214,106 describes a process for preparing ethylene glycol starting from glycolic acid. The reaction is carried out over Pd/Re, Pd/Ag, Ru/Rh, Pd/Au, Re/Ag, Pt/Rh or Pd/Re/Ag catalysts at from 145 to 241° C.

The known catalysts have insufficient activities or selectivities in some applications.

Furthermore, the use of carboxylic acids, in particular in the form of aqueous solutions, entails the risk of corrosion of the materials of construction of the equipment contacting the carboxylic acids, for example reaction vessels. For this reason, either very thick steels or noble and thus costly materials have to be used for the equipment. Accordingly, there is a need for a process in which the problem of corrosion is significantly reduced.

It is an object of the present invention to provide a process for preparing aliphatic alcohols by hydrogenating aliphatic carboxylic acids or anhydrides or esters thereof or lactones in the presence of a catalyst comprising Pt and Re, in the form of the metal or an oxide in each case, without the disadvantages of existing processes.

We have found that this object is achieved by using a catalyst comprising Pt and Re, in the form of the metal or an oxide in each case, and at least one further element from groups 5 to 12 and 14 and the lanthanides of the Periodic Table of the Elements in the form of the metal or an oxide.

The present invention further provides such a catalyst and its use for hydrogenating aliphatic carboxylic acids or anhydrides and esters thereof or lactones.

The inventors have found that, using the catalyst of the invention, the abovementioned reaction may be carried out at low temperatures, preferably of at most 200° C., which leads to a very strong reduction in the problem of corrosion in the equipment.

The catalyst of the invention comprises or, in particular, consists of Pt, Re and at least one further element from groups 5 to 12 and 14 and the lanthanides of the Periodic Table of the Elements (IVth main group, Ist, IInd, Vth, VIth, VIIth, VIIIth transition group of the Periodic Table of the Elements), in the form of the metal or an oxide in each case, optionally on a support.

The present invention further provides a catalyst obtainable by reducing an aqueous suspension and/or solution of oxides, oxide hydrates, carbonates, nitrates, carboxylates, chelates, sulfates, phosphates and/or halides of Pt, Re and at least one further element from groups 5 to 12 and 14 and the lanthanides of the Periodic Table of the Elements.

The at least one further element is preferably selected from groups 6, 10 and 11 of the Periodic Table of the Elements. It is used in the form of the metal or an oxide. Particular preference is given to the elements Sn, V, Cr, Mo, W, Mn, Fe, Ru, Os, Co, Ni, Pd, Cu, Ag, Au, Zn, La and Ce. Especially preferred are Mo, Ag, Au and/or Pd in the form of the metal or an oxide. In one embodiment of the invention, the catalyst includes only one further element in the form of the metal or an oxide.

The catalyst may be employed as unsupported or supported catalyst. For use as supported catalyst, all suitable support materials may be employed, for example active carbons, $SiO_2$, $Al_2O_3$, $TiO_2$, $ZrO_2$, clays such as montmorillonites, zeolites or mixtures thereof. The catalyst can be prepared in various ways. The catalyst is obtainable, for example, by reducing an aqueous suspension and/or solution of oxides, oxide hydrates, carbonates, nitrates, carboxylates, chelates, in particular with 1,3-diketo compounds, sulfates, phosphates and/or halides of Pt, Re and at least one further element from the groups 5 to 12 and 14 and the lanthanides of the Periodic Table of the Elements. The catalysts can be prepared by initially charging all of the components and reducing the initial charge, preferably with hydrogen. However, the reduction can also be carried out sequentially. In this case, the activation or reduction of the catalyst or catalyst precursors is preferably carried out at from 200 to 500° C., particularly preferably at from 210 to 400° C., in particular at from 220 to 300° C. Following the reduction, the catalysts are often not present, or are present only to a minor extent, in the form of intermetallic compounds.

For example, $PtO_2$, an Re compound such as $Re_2O_7$ and at least one additional compound of the third component are introduced into water and reduced with hydrogen. The catalyst obtained in this way can be directly employed for the hydrogenation. Supported catalysts can be prepared, for example, in such a way that platinum oxide or platinum oxide hydrate are already present on the support, it being possible to prepare the Pt/support mixture by impregnation or coprecipitation of platinum oxide precursor or platinum oxide hydrate precursor and support material and subsequent calcination. The Re compounds and the further component can also be added by impregnation or precipitation. It is possible, for example, for the platinum oxide or platinum oxide hydrate to have been reduced on the support previously.

The ratio by weight of Pt to Re or of Pt to the at least one further element is preferably 100–0.01, particularly preferably 50–0.05, in particular 10–0.1.

Pt is preferably employed in oxide or oxide hydrate form before reduction or activation. The Pt component is preferably present in the form of $PtO_2$. Re sources that can be used are customary Re compounds; $Re_2O_7$ is preferably used.

The catalysts may be prepared in the form of powders or shaped bodies such as extrudates, tablets, pellets, or as a fixed bed.

In principle, all aliphatic carboxylic acids or anhydrides or esters thereof or lactones can be hydrogenated in the process of the invention to give aliphatic alcohols.

The aliphatic carboxylic acid preferably contains at least 3 carbon atoms, particularly preferably at least 4 carbon atoms. The number of carbon atoms refers to the individual acid and includes the carboxyl groups. Derivatives of the carboxylic acid have correspondingly more carbon atoms.

In one embodiment, the carboxylic acid does not contain any OH groups adjacent to the carboxyl groups or any hydroxyl groups at all.

The number of carboxyl groups in the carboxylic acid is not critical. Mono-, di-, tri- or tetracarboxylic acids are usually employed, particularly preferably mono- or dicarboxylic acids.

The number of carbon atoms in the carboxylic acid is also uncritical. The carboxylic acid contains preferably from 3 to 30, in particular from 4 to 20, especially from 4 to 10, carbon atoms. The aliphatic moiety may be linear or branched. It may contain one or more double and/or triple bonds in its skeleton.

Customary anhydrides or esters can be employed in the process of the invention instead of the free carboxylic acid.

Examples of suitable carboxylic acids are monocarboxylic acids such as propionic acid, butyric acid, pentanoic acid, hexanoic acid, pentadecanoic acid, hexadecanoic acid, heptadecanoic acid and octadecanoic acid. The monocarboxylic acids may be unsaturated. Examples of suitable dicarboxylic acids are succinic acid, fumaric acid, maleic acid and adipic acid.

Examples of lactones are butyrolactone, methylbutyrolactones or caprolactone.

Double or triple bonds, if present in the skeleton, are cohydrogenated in the hydrogenation to give the saturated compounds. Carbonyl groups, if present, are hydrogenated as well.

The resulting alcohols have many uses, for example as solvents, intermediates or alcohol components for polymers.

Dicarboxylic acids can be employed in the hydrogenation in undiluted form or in solution or in suspension. Suitable solvents include all substances which are inert under the reaction conditions, such as water, dioxane, tetrahydrofuran, ethylene glycol ethers, hydrocarbons such as hexane or alcohols such as methanol, ethanol, or the reaction product itself. Preferably employed as solvents are water and/or alcohols produced in the reaction. In the hydrogenation of butyric acid, for example, butanol is used. The hydrogenation can be carried out continuously or batchwise. If the process is carried out batchwise, the catalyst may be employed, for example, in the form of a powder. If the process is carried out continuously, the catalyst may be arranged as a fixed bed, and the process can be provided with product recycling.

The hydrogenation temperature is preferably at most 200° C. Hydrogenation temperatures are preferably from 30 to 200° C., particularly preferably 100 to 185° C., in particular 120 to 170° C. The reaction pressure is usually regulated with hydrogen and is preferably from 1 to 350 bar. The pressure for reaction in the gas phase is preferably from 1 to 80 bar, and for reaction in the liquid phase it is preferably from 20 to 330 bar, particularly preferably 100 to 300 bar.

The hydrogenation may be carried out in the presence of water.

In the hydrogenation of aliphatic dicarboxylic acids or anhydrides or esters thereof in the presence of the catalyst of the invention, lactones may be formed by ring-closure in addition to aliphatic diols. The diol or lactone selectivity can be controlled by appropriate selection of the at least one further element of the catalyst. If cobalt acetate, for example, is used as a source of the further element, methylbutyrolactones are formed predominantly in the reduction of itaconic acid. If palladium acetate is used as a source for the further element, 2-methylbutanediol is formed predominantly.

The Examples which follow illustrate the invention.

EXAMPLES

Example 1

0.1 g of $PtO_2$, 0.2 g of $Re_2O_7$, 0.1 g of silver acetate and 9 g of water were introduced into a metal autoclave. Then 60 bar of hydrogen were injected, and the mixture was heated to 270° C. with stirring. After one hour, the mixture was cooled to room temperature, the autoclave was decompressed, and 1 g of adipic acid was added. Then 100 bar of hydrogen were injected, and the mixture was heated to 150° C. with stirring. After 2 hours, cooling and decompression were again carried out. The effluent of the reaction was analyzed by gas chromatography. 81.3% of 1,6-hexanediol was found, with complete adipic acid conversion. The remainder consisted of n-hexanol, 6-hydroxycaproic acid and the ester of hexanediol and hydroxycaproic acid.

Example 2

Itaconic acid was hydrogenated as in Example 1. 45.2% of 2-methylbutanediol and 47.9% of methylbutyrolactones were found in the effluent of the reaction, with 100% conversion. The remainder consisted predominantly of 3-methyltetrahydrofuran, 2-methylbutanol and 3-methylbutanol.

Example 3

Cobalt acetate was used for a catalyst preparation as in Example 2 instead of silver acetate. Following hydrogenation as in Example 2, 17.1% of 2-methylbutanediol and 75.6% of methylbutyrolactones were found in the effluent of the reaction. The remainder consisted predominantly of 3-methyltetrahydrofuran, 2-methylbutanol and 3-methylbutanol.

Example 4

Triphenylphosphinegold nitrate was used for a catalyst preparation as in Example 2 instead of silver acetate. Following hydrogenation as in Example 1, 62.5% of 2-methylbutanediol and 24.4% of methylbutyrolactones were found in the effluent of the reaction. The remainder consisted predominantly of 3-methyltetrahydrofuran, 2-methylbutanol and 3-methylbutanol.

Example 5

Palladium acetate was used for a catalyst preparation as in Example 2 instead of silver acetate. Following hydrogenation as in Example 2, 76.7% of 2-methylbutanediol and 1.8% of methylbutyrolactones were found in the effluent of the reaction. The remainder consisted predominantly of 3-methyltetrahydrofuran, 2-methylbutanol and 3-methylbutanol.

Example 6

Molybdenum trioxide was used for a catalyst preparation as in Example 2 instead of silver acetate. Following hydrogenation as in Example 2, 73.3% of 2-methylbutanediol and 8.8% of methylbutyrolactones were found in the effluent of the reaction. The remainder consisted predominantly of 3-methyltetrahydrofuran, 2-methylbutanol and 3-methylbutanol.

Example 7

Maleic acid was hydrogenated at 140° C. as in Example 1. 70% of 1,4-butanediol were found in the effluent of the reaction, with 100% conversion. The remainder consisted predominantly of tetrahydrofuran, gamma-butyrolactone, 4-hydroxybutyraldehyde and butanol.

We claim:

1. A process for preparing aliphatic by diols or lactones by hydrogenating aliphatic dicarboxylic acids having at least 3 carbon atoms, or anhydrides or esters thereof in the presence of a catalyst comprising Pt and Re, in the form of the metal or an oxide in each case, wherein the catalyst further comprises at least one further element from groups 5 to 12 and 14 and the lanthanides of the Periodic Table of the Elements, with the exception of palladium, in the form of the metal or an oxide.

2. A process as claimed in claim 1, wherein the at least one further element is at least one element from groups 6, 10 and 11 of the Periodic Table of the Elements in the form of the metal or an oxide.

3. A process as claimed in claim 1, wherein the catalyst comprises Mo, Ag and/or Au in the form of the metal or an oxide in each case.

4. A process as claimed in claim 1, wherein the hydrogenation temperature is at most 200° C.

5. A process as claimed in claim 1, wherein the hydrogenation is carried out in the presence of water.

6. A process as claimed in claim 1, wherein the Pt component is present in the form of $PtO_2$ prior to reduction with hydrogen.

7. A process as claimed in claim 2, wherein the dicarboxylic acid is selected from the group consisting of succinic acid, fumaric acid, maleic acid, itaconic acid, and adipic acid.

* * * * *